United States Patent [19]

Tawada et al.

[11] 4,102,881
[45] Jul. 25, 1978

[54] BENZODIAZEPINE DERIVATIVES

[75] Inventors: Hiroyuki Tawada, Kyoto; Hideaki Natsugari, Osaka; Kanji Meguro; Yutaka Kuwada, both of Hyogo, all of Japan

[73] Assignee: Takeda Chemical Industries, Ltd., Osaka, Japan

[21] Appl. No.: 478,823

[22] Filed: Jun. 12, 1974

Related U.S. Application Data

[63] Continuation of Ser. No. 128,507, Mar. 26, 1971, abandoned.

[30] Foreign Application Priority Data

| Mar. 27, 1970 | [JP] | Japan | 50-25804 |
| Mar. 27, 1970 | [JP] | Japan | 50-25805 |
| Apr. 23, 1970 | [JP] | Japan | 50-34950 |
| May 28, 1970 | [JP] | Japan | 50-46637 |

[51] Int. Cl.$^2$ ............................................. C07D 243/48
[52] U.S. Cl. ....................... 260/239 BD; 268/453 RW
[58] Field of Search ......... 260/239 BD; 268/453 RW

[56] References Cited

U.S. PATENT DOCUMENTS

| 3,462,418 | 8/1969 | Archer et al. | 260/239.3 D |
| 3,520,878 | 5/1970 | Peterson | 260/239.3 D |

OTHER PUBLICATIONS

Standinger, et al., "Helvitica Chem. Acta.", vol. IV, pp. 861–886, (1921).
Kosolapoff, et al., (J), "Organic Phosphorous Compounds", vol. 3, Wiley, (1972), pp. 71, 72, 81, 82.
Kosolapoff, et al., (II), "Organic Phosphorous Compounds", vol. 1, Wiley, (1972), p. 82.

*Primary Examiner*—Donald G. Daus
*Assistant Examiner*—D. B. Springer
*Attorney, Agent, or Firm*—Wenderoth, Lind & Ponack

[57] ABSTRACT

Compounds of the formula

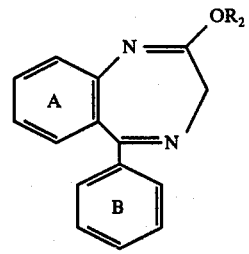

wherein $R_2$ is lower alkyl and each of rings A and B is unsubstituted or substituted by a member selected from the group consisting of nitro, trifluoromethyl, halogen, alkyl and alkoxy, and processes for their preparation.

3 Claims, No Drawings

BENZODIAZEPINE DERIVATIVES

This is a continuation, of application Ser. No. 128,507, filed Mar. 26, 1971, now abandoned.

This invention relates to novel benzodiazepine derivatives of the general formula

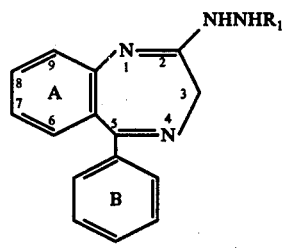

(wherein $R_1$ is hydrogen or acyl group and each of the rings A and B has no substituents or has one or more substituents selected from nitro, trifluoromethyl, halogen, alkyl and alkoxy) and pharmaceutically acceptable acid salts thereof.

The compounds (I) and pharmaceutically acceptable acid salts thereof are useful, for example, as tranquilizers, muscle relaxants, sedatives or anti-convulsants and also useful as intermediates for production of triazolobenzodiazepine derivatives showing medicinal effects similar to the above.

The principal object of the present invention is to provide novel and useful compounds (I).

The second object is to provide a novel and useful process for the production of the compounds (I).

The third object is to provide novel compounds of the general formula

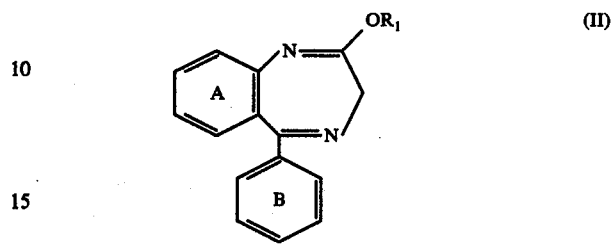

(wherein $R_2$ is lower alkyl group and the rings A and B have the meaning as defined above), which are useful as starting materials for the production of the compounds (I).

The fourth object is to provide a novel process for the production of the compounds (II).

Reactions concerning the present invention are summarized in the following scheme:

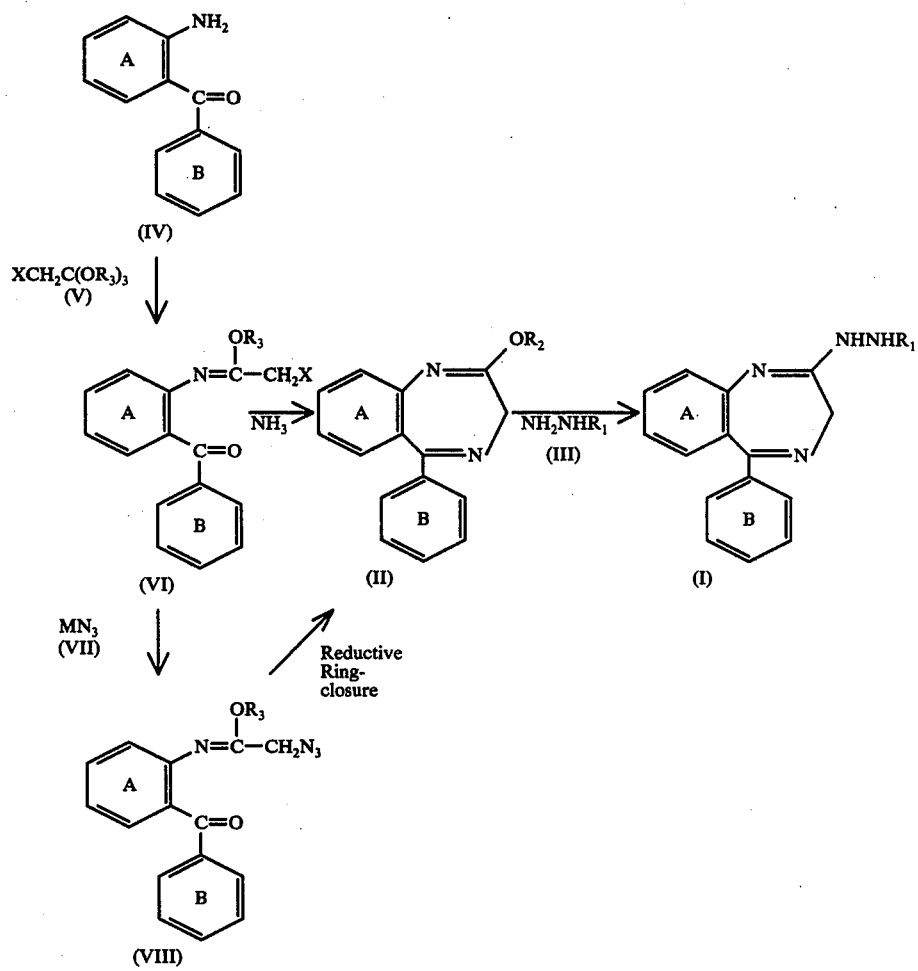

(wherein $R_3$ is lower alkyl defined by $R_2$, X is halogen, M is alkali metal, and others have the meanings defined above)

Referring to the general formulas, the acyl group represented by $R_1$ may be any of ones derived from aliphatic, aromatic and aromato-aliphatic carboxylic acids. Preferable acyl derived from aliphatic carboxylic acid is one having up to 7 carbon atoms which is exemplified by formyl, acetyl, propionyl, iso-propionyl, butyryl, iso-butyryl, sec-butyryl, tert-butyryl, valeryl, hexanoyl or enanthyl. Preferable acyl derived from aromatic carboxylic acid may be, for example, benzoyl, toluoyl or chlorobenzoyl. The acyl derived from aromato-aliphatic carboxylic acid may be, for example, phenylacetyl or phenylpropionyl.

The halogen which may be substituted on each of the rings A and B includes chlorine, bromine, fluorine, iodine.

The alkyl which may be substituted on each of the rings A and B is preferably one having up to 4 carbon atoms such as methyl, ethyl, propyl, iso-propyl, butyl, sec-butyl, or tert-butyl.

The alkoxy which may be substituted on each of the rings A and B is preferably one having up to 4 carbon atoms such as methoxy, ethoxy, propoxy, iso-propoxy, butoxy, sec-butoxy or tert-butoxy. The lower alkyl represented by $R_2$ and $R_3$ is preferably one having up to 4 carbon atoms such as methyl, ethyl, propyl, iso-propyl, butyl, sec-butyl or tert-butyl.

Halogen represented by X may, for example, be chlorine, bromine or iodine.

Alkali metal represented by M may, for example, be lithium, sodium or potassium.

The principal and the second objects of the present invention are realized by allowing a compound of the general formula

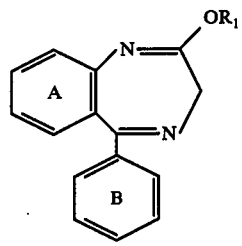  (II)

(wherein all the symbols have the meanings defined above) to react with a compound of the general formula

 (III)

(wherein $R_1$ has the meaning defined above), whereby the objective compound of the general formula

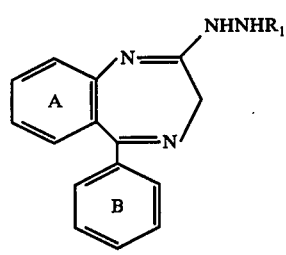 (I)

(wherein all the symbols have the meanings defined above) is produced.

The present reaction is generally conducted at room temperature in the presence of a solvent (e.g. alcohol such as methanol or ethanol) and may be accelerated by the addition of an acid such as acetic acid, propionic acid, hydrochloric acid, sulfuric acid, etc. The reaction temperature may be suitably controlled lower or higher than room temperature, if desired.

An amount of the compound (III) employed is practically about one mole to about ten moles per mole of the compound (II).

In this manner, the compound (I) is produced and can be isolated in a form of free base or its acid salt (e.g. hydrochloride, sulfate) by per se conventional separation or purification means (e.g. extraction, distillation, recrystallization, chromatography).

The starting compound (II) of the present invention can be produced by allowing a compound of the general formula

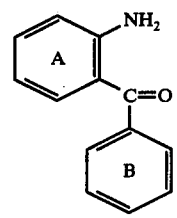 (IV)

(wherein all the symbols have the meanings defined above) to react with a compound of the general formula

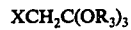 (V)

(wherein X is halogen and $R_3$ is lower alkyl), whereby a compound of the general formula

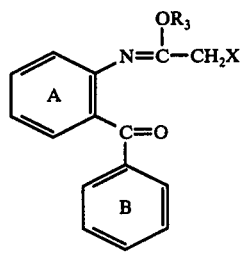 (VI)

(wherein all the symbols have the meanings defined above) is produced, allowing the compound (VI) to react with a compound of the general formula

 (VII)

(wherein M is alkali metal), whereby a compound of the general formula

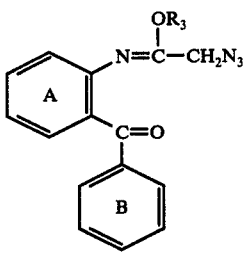 (VIII)

(wherein all the symbols have the meanings defined above) is produced, and finally subjecting the compound (VIII) to a reductive ring-closure reaction, whereby the compound (II) is produced.

Detailed explanation will be made hereinafter with respective steps for the production of the compound (II).

In the first step, the compound (IV) is allowed to react with the compound (V) to produce the compound (VI).

The present reaction is generally conducted in the absence or in the presence of a suitable solvent (e.g. benzene, toluene, xylene, carbon tetrachloride, chloroform, methylenechloride) at a suitable temperature ranging from room temperature to a boiling point of the solvent used. The present reaction may be accelerated by the addition of an acid (e.g. organic acid such as acetic acid, inorganic acid such as hydrochloric acid and sulfuric acid).

An amount of the compound (V) employed is practically about one mole to about five moles per mole of the compound (IV).

In the subsequent step, the compound (VI) is allowed to react with the compound (VII) to produce the compound (VIII). This reaction is generally conducted in the presence of a suitable solvent (e.g. alcohol such as methanol and ethanol, dimethylformamide) at room temperature. The reaction temperature may be suitably controlled lower or higher than room temperature.

An amount of the compound (VII) employed is practically about one mole to about two moles per mole of the compound (VI).

In the subsequent step, the compound (VIII) is subjected to a reductive ring-closure reaction to produce the compound (II).

The reductive ring-closure is accomplished by keeping the compound (VIII) under such condition as enabling an azido group to be reduced into an amino group, whereby the azido group of the compound (VIII) is reduced to an amino group and the ring closure takes place successively. The conditions mentioned just above may be any of conventional ones. For example, a reducing agent such as Raney nickel zinc, iron may be allowed to act upon the compound (VIII), or the compound (VIII) may be kept under catalytic reduction conditions. Upon conducting this reaction, a solvent (e.g. alcohol such as methanol and ethanol) may be used, and the reaction system may preferably be kept under neutral or slight alkaline conditions at a temperature ranging from room temperature to a boiling point of the solvent used.

The intermediate produced in the course of the reaction is shown by the general formula

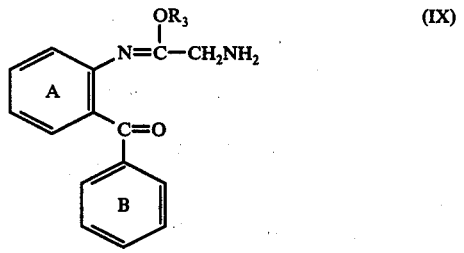

(IX)

(wherein all the symbols have the meanings defined above).

The present reductive ring-closure reaction is also accomplished by allowing the compound (VIII) to react with trisubstituted phosphine derivatives of the general formula

P(R$_4$)$_3$  (X)

(wherein R$_4$ is alkyl (e.g. methyl, ethyl, propyl, butyl), aralkyl (e.g. benzyl) or aryl (e.g. phenyl)). This reaction is generally conducted in the presence of a suitable solvent (e.g. benzene, toluene). The reaction temperature is generally room temperature and optionally may be controlled higher or lower than room temperature. An amount of the compound (X) employed is practically about equimolar or a little excess per mole of the compound (VIII). This reductive ring-closure reaction is recommended particularly, when a group sensitive to reduction (e.g. nitro) is present in the compound (VIII).

In this reaction, a compound of the general formula

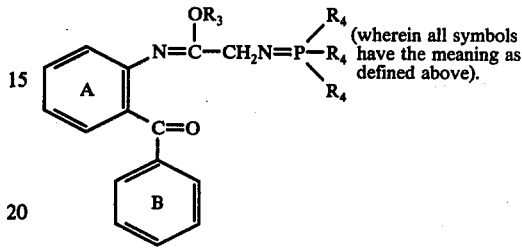

(wherein all symbols have the meaning as defined above).

is assumed to be produced as an intermediate.

The compound (II) is also produced by allowing the compound (VI) to react with ammonia. The reaction is generally conducted in the presence of a suitable solvent (e.g. methanol, ethanol, chloroform, dichloromethane, dioxane, dimethylformamide, a mixture of them) at room temperature or lower. The reaction may be accelerated with heating as desired. The reaction is advantageously conducted in a sealed vessel to prevent ammonia from vaporization.

In the present reaction, since the compound (VI) wherein X is iodine is generally more reactive than the compound (VI) wherein X is chlorine or bromine, it may sometimes be advisable to conduct the reaction after converting the chloro- or bromo derivatives into the iodo derivative by treating the former with sodium or potassium iodide. Alternatively, it may be advisable to conduct the reaction in the presence of sodium iodide or potassium iodide together with the compound (VI) wherein X is chlorine or bromine.

In the course of the present reaction, the compound (IX) previously described is considered to be produced as an intermidiate.

In this manner, the compound (II) is produced and can be isolated by per se conventional means (e.g. distillation of the reaction mixture to remove the solvent and ammonia, extraction of the residue with a suitable solvent (such as ether, benzene, ethyl acetate and chloroform).

The compounds (I) and the compounds (II) as well as their pharmaceutically acceptable acid salts are novel compounds and useful, for example, as tranquilizers, sedatives, anti-convulsants or muscle relaxants.

Those compounds are administered in a form of a suitable conventional pharmaceutical composition such as powder, granules, tablets, injection solution together with pharmaceutically acceptable carriers or adjuvants. Although the dose of those compounds varies with the kinds of the compounds, severity of the disease, etc., it falls generally within a range of about 1 to 30 milligrams for adult human per day.

Furthermore, the compound (I) can be converted to a novel triazolobenzodiazepine derivative which is useful as a medicine showing strong pharmacological effect by the following reaction:

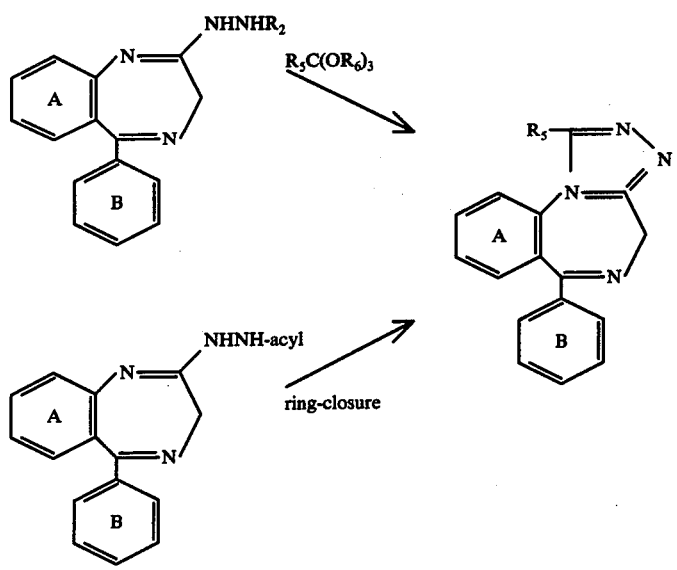

In the formulas $R_5$ is hydrogen, alkyl, aralkyl or aryl and $R_6$ is lower alkyl.

The novel triazolobenzodiazepine derivatives of the above general formula are also effective as tranquilizers, sedatives, muscle relaxants or anticonvulsants when administered in a similar dose and pharmaceutical composition to those of the compound (I).

The following are Examples of and References for the present invention, wherein the term "parts(s)" means weight part(s) unless specified and the relation between "part(s)" and "part by volume(s)" corresponds to that between gram(s) and milliliter(s).

Production of the compound (II)

EXAMPLE 1

(1) To a solution of 11.5 parts of 2-amino-5-chlorobenzophenone in 150 parts by volume of benzene are added 18 parts of ethyl orthobromoacetate and 9 parts by volume of acetic acid. The mixture is refluxed for 2 hours. The reaction mixture is washed with an aqueous solution of sodium carbonate and water, and dried over anhydrous sodium sulfate. The solvent is distilled off under reduced pressure. The residue is treated with petroleum ether to give 2-(2-bromo-1-ethoxyethylideneamino)-5-chlorobenzophenone as crystals.

The product is recrystallized from n-hexane to give pale yellow needles melting at 72°–73° C.

| Elementary Analysis | | | |
|---|---|---|---|
| Calculated for $C_{17}H_{15}BrClNO_2$ | C 53.63, | H 3.97, | N 3.68 |
| Found | C 53.56, | H 3.91, | N 3.67 |

(2) To a solution of 3.8 parts of 2-(2-bromo-1-ethoxyethylideneamino)-5-chlorobenzophenone produced in Step (1) in 30 parts by volume of dimethylformamide is added 0.72 part of sodium azide. The mixture is heated at 80° C for 10 minutes, and is poured into 60 parts by volume of ice water. The resulting oily precipitate is extracted with ethyl acetate. Ethyl acetate layer is washed with water and dried over anhydrous sodium sulfate. After evaporation of the solvent, 2-(2-azido-1-ethoxyethylideneamino)-5-chlorobenzophenone is obtained quantitatively as an oily substance. The product shows an absorption band at 2100 cm$^{-1}$ due to $N_3$ in an infrared absorption spectrum.

(3) To a solution of 0.35 part of 2-(2-azido-1-ethoxyethylideneamino)-5-chlorobenzophenone produced in Step (2) in 10 parts by volume of ethanol is added 2 parts by volume of Raney nickel washed sufficiently with ethanol. The mixture is refluxed for 25 minutes and filtered to remove the Raney nickel. The filtrate is evaporated under reduced pressure and 7-chloro-2-ethoxy-5-phenyl-3H-1,4-benzodiazepine is obtained as an oily substance.

The nuclear magnetic resonance spectrum and other physicochemical data support the structural formula of the product. When the product is treated with methanolic hydrogenchloride, 7-chloro-1,3-dihydro-5-phenyl-2H-1,4-benzodiazepin-2-one is obtained as crystals melting at 211°–213° C.

EXAMPLE 2

To a solution of 1.7 part of 2-(2-azido-1-ethoxyethylideneamino)-5-chlorobenzophenone produced in Step (2) of Example 1 in 50 parts by volume of methanol is added a solution of 1.6 part of ammonium chloride in 5 parts by volume of water. To the mixture is added 1 part of zinc powder with stirring. After 10 minutes, the resulting precipitates are removed by filtration. The filtrate is poured into 100 parts by volume of water, and extracted with ethyl acetate. Ethyl acetate layer is washed with water and dried over anhydrous sodium sulfate. The solvent is distilled off under reduced pressure to give 7-chloro-2-ethoxy-5-phenyl-3H-1,4-benzodiazepine as an oily substance.

The product coincides perfectly with that obtained in Example 1 in an infrared absorption spectrum and nuclear magnetic resonance spectrum.

EXAMPLE 3

(1) To a solution of 2.42 parts of 2-amino-5-nitrobenzophenone in 40 parts by volume of benzene are added 9.64 parts of ethyl orthobromoacetate and 3 parts of acetic acid, followed by refluxing for 7 hours. The reaction mixture is washed with a saturated aqueous sodium bicarbonate solution and water, and dried over anhydrous sodium sulfate. After evaporation of the solvent under reduced pressure, 2-(2-bromo-1-ethoxyethylideneamino)-5-nitrobenzophenone is obtained as an oily substance.

(2) To a solution of 3.3 parts of 2-(2-bromo-1-ethoxyethylideneamino)-5-nitrobenzophenone produced in Step (1) in 15 parts by volume of dimethylformamide is added 0.5 part of sodium azide at a room temperature with stirring. After the stirring is continued for further 40 minutes. Ethyl acetate and water are added to the reaction mixture and shaken well. The ethyl acetate layer separated is washed with water and dried over anhydrous sodium sulfate. Evaporation of the solvent gives 2-(2-azido-1-ethoxyethylideneamino)-5-nitrobenzophenone as an oily substance. The product shows an absorption band at 2077 cm$^{-1}$ due to N$_3$ in an infrared absorption spectrum.

(3) To a solution of 2.5 parts of 2-(2-azido-1-ethoxyethylideneamino)-5-nitrobenzophenone produced in Step (2) in 30 parts by volume of benzene is added with stirring 1.78 parts of triphenylphosphine. The mixture is stirred for further 1.5 hours and the solvent is removed by distillation. The residue is extracted with a mixture of n-hexane and acetone (7:3), and the soluble fraction is purified by means of chromatography employing Silica Gel, whereupon 2-ethoxy-7-nitro-5-phenyl-3H-1,4-benzodiazepine is obtained as pale yellow crystals. Recrystallization from ether-n-hexane gives pale yellow prisms melting at 143°–145° C.

Elementary Analysis
Calculated for C$_{17}$H$_{15}$N$_3$O$_3$

|  | C | H | N |
|---|---|---|---|
| Calculated | C 66.01, | H 4.89, | N 13.59 |
| Found | C 66.13, | H 4.81, | N 13.63 |

EXAMPLE 4

To a solution of 1.3 parts of 2-amino-5-chloro-4'-methoxybenzophenone in 20 parts by volume of benzene are added 1.8 parts of ethyl orthobromoacetate and 0.9 part by volume of acetic acid. The mixture is refluxed for 1 hour. The reaction mixture is washed with a saturated aqueous sodium bicarbonate solution and water, and dried over anhydrous sodium sulfate. The solvent is distilled off under reduced pressure. Subsequently, the resulting 2-(2-bromo-1-ethoxyethylideneamino)-5-chloro-4'-methoxybenzophenone is dissolved in 15 parts by volume of dimethylformamide, followed by addition of 0.36 part of sodium azide. The mixture is heated at 80° C for 5 minutes. The reaction mixture is poured into 40 parts by volume of water, and extracted with ethyl acetate. Ethyl acetate layer is washed with water and dried over anhydrous sodium sulfate. Evaporation of the solvent gives 2-(2-azido-1-ethoxyethylideneamino)-5-chloro-4'-methoxybenzophenone. To a solution of the resulting product in 50 parts by volume of methanol is added 1.6 parts of ammonium chloride in 5 parts by volume of water. To the mixture is added 1 part of zinc powder portionwise with stirring. After 20 minutes, the resulting precipitates are removed by filtration. Filtrate is concentrated up to half volume and the resultant is extracted with ethyl acetate. Ethyl acetate layer is washed with water and dried over anhydrous sodium sulfate, followed by distillation of the solvent. The residue is treated with isopropyl ether, whereupon 7-chloro-2-ethoxy-5-(4-methoxyphenyl)-3H-1,4-benzodiazepine is obtained as crystals. The product is recrystallized from isopropyl ether to give colorless prisms melting at 119°–120° C.

Elmentary Analysis
Calculated for C$_{18}$H$_{17}$ClN$_2$O$_2$

|  | C | H | N |
|---|---|---|---|
| Calculated | C 65.75, | H 5.21, | N 8.52 |
| Found | C 65.96, | H 5.32, | N 8.44 |

EXAMPLE 5

A mixture of a solution of 0.38 part of 5-chloro-2-(2-bromo-1-ethoxyethylideneamino)benzophenone in 8 parts by volume of methylenechloride and 2 parts by volume of liquid ammonia is stirred in a sealed vessel at room temperature for 1 hour, followed by evaporation at room temperature to remove the ammonia. The resultant is shaken well with a mixture of 10 parts by volume of methylenechloride and 5 parts by volume of water. The methylene chloride layer is washed with water and dried over sodium sulfate, followed by evaporation of the solvent gives 7-chloro-2-ethoxy-5-phenyl-3H-1,4-benzodiazepine as an oily substance.

This substance is identical with the product prepared in Examples 1 and 2.

EXAMPLE 6

To a solution of 3.8 parts of 5-chloro-2-(2-bromo-1-ethoxyethylideneamino)benzophenone in 30 parts by volume of acetone is added with stirring a solution of 1.5 parts of sodium iodide in 12 parts by volume of acetone. After about one hour, the resulting precipitate is removed by filtration. The filtrate is concentrated under reduced pressure. The concentrate is treated with petroleum ether to give 5-chloro-2-(1-ethoxy-2-iodoethylideneamino)benzophenone as crystals. The crystals are recrystallized from n-hexane to give pale brown pillars melting at 67°–68° C.

A mixture of a solution of 0.12 part of 5-chloro-2-(1-ethoxy-2-iodoethylideneamino)benzophenone in 6 parts by volume of methylenechloride and 1.5 parts by volume of liquid ammonia is stirred in a sealed vessel at room temperature for 1 hour. The reaction mixture is treated after the manner described in the preceding Example, whereupon 7-chloro-2-ethoxy-5-phenyl-3H-1,4-benzodiazepine is given as an oily substance.

Production of the compound (I)

EXAMPLE 7

To a solution of 0.3 part of 7-chloro-2-ethoxy-5-phenyl-3H-1,4-benzodiazepine in 10 parts by volume of methanol is added 0.5 part of hydrazine hydrate (100%) and 0.06 part by volume of acetic acid. The mixture is stirred at room temperature for 1.5 hours. The reaction mixture is poured into 30 parts by volume of water, and extracted with chloroform. Chloroform layer is washed with water and dried over anhydrous sodium sulfate. After evaporation of the solvent, the residue is treated with benzene, whereupon 7-chloro-2-hydrazino-5-phenyl-3H-1,4-benzodiazepine is obtained as colorless crystals melting at 203°–205° C.

EXAMPLE 8

To a solution of 0.25 part of 2-ethoxy-7-nitro-5-phenyl-3H-1,4-benzodiazepine in 8 parts by volume of methanol is added 0.2 part by volume of hydrazine hydrate (100%) with stirring and the stirring is continued at room temperature for further 2.5 hours. To the reaction mixture is added water, followed by extraction with chloroform. Chloroform layer is washed with water and dried over anhydrous sodium sulfate, followed by distillation of the solvent. Treatment of the residue with n-hexane gives 2-hydrazino-7-nitro-5-phenyl-3H-1,4-benzodiazepine as orange crystalline powder. The product is treated with acetone, whereupon 2-(2-isopropylidenehydrazino)-7-nitro-5-phenyl-3H-1,4-benzodiazepine is obtained as pale yellow crystals melting at 203°–205° C.

| Elementary Anaalysis | | | |
|---|---|---|---|
| Calculated for $C_{18}H_{17}N_5O_2$ | C 64.46, | H 5.11, | N 20.89 |
| Found | C 64.33, | H 5.15, | N 20.89 |

EXAMPLE 9

To a solution of 0.24 part of 7-chloro-2-ethoxy-5-phenyl-3H-1,4-benzodiazepine in 10 parts by volume of methanol are added 0.6 part of acetylhydrazine and 0.05 part by volume of acetic acid. The mixture is stirred at room temperature for 6 hours, and concentrated up to half volume. The resulting precipitate is collected by filtration and washed with ethanol and ether, whereupon 2-acetylhydrazino-7-chloro-5-phenyl-3H-1,4-benzodiazepine is obtained as crystals melting at 205°–206° C.

EXAMPLE 10

To a solution of 0.11 part of 7-chloro-2-ethoxy-5-(4-methoxyphenyl)-3H-1,4-benzodiazepine in 5 parts by volume of methanol is added 0.2 part by volume of hydrazine hydrate (100%). The mixture is stirred at room temperature for 1.5 hours, and poured into 20 parts by volume of water. The mixture is extracted with chloroform. Chloroform layer is washed with water and dried over anhydrous sodium sulfate. The solvent is distilled off. Treatment of the residue with benzene gives 7-chloro-2-hydrazino-5-(4-methoxyphenyl)-3H-1,4-benzodiazepine as crystals melting at 213°–215° C.

In a similar manner to that in Example 7, 8, 9 or 10, the following compounds (I) are produced.

7-Chloro-2-(2-formylhydrazino)-5-phenyl-3H-1,4-benzodiazepine melting at 161°–162° C (adduct of ½ mole of methanol).

7-Chloro-5-phenyl-2-(2-propionylhydrazino)-3H-1,4-benzodiazepine melting at 186°–187° C. (eff.).

7-Chloro-2-(2-enanthylhydrazino)-5-phenyl-3H-1,4-benzodiazepine melting at 224°–225° C (eff.).

2-(2-Benzoylhydrazino)-7-chloro-5-phenyl-3H-1,4-benzodiazepine melting at 207°–208° C (eff.).

2-(2-Phenylacetylhydrazino)-5-phenyl-3H-1,4-benzodiazepine melting at 224°–225° C (eff.).

2-(2-Acetylhydrazino)-7-nitro-5-phenyl-3H-1,4-benzodiazepine melting at 184°–185° C (eff.).

Production of triazolobenzodiazepine derivatives

Reference 1

To a solution of 2.0 parts of 7-chloro-2-hydrazino-5-phenyl-3H-1,4-benzodiazepine and 7.4 parts of ethyl orthoformate in 80 parts by volume of chloroform is added 2 parts of concentrated sulfuric acid with stirring. The mixture is stirred at room temperature for further 30 minutes, and neutralized with a saturated aqueous sodium bicarbonate solution. Chloroform layer is washed with water and dried over sodium sulfate, followed by distillation of the solvent. Recrystallization of the residue from acetone-n-hexane yields 8-chloro-6-phenyl-4H-s-triazolo-[4,3-a][1,4]benzodiazepine as colorless flakes melting at 226°–227° C.

| Elementary Analysis | | | |
|---|---|---|---|
| Calculated for $C_{16}H_{11}ClN_4$ | C 65.20, | H 3.76, | N 19.01 |
| Found | C 65.30, | H 3.48, | N 19.03 |

REFERENCE 2

To a suspension of 2.84 parts of 7-chloro-2-hydrazino-5-phenyl-3H-1,4-benzodiazepine in a mixture of 100 parts by volume of ethanol and 5 parts by volume of ethyl orthoacetate is added 1 part of concentrated sulfuric acid with stirring. The mixture is further stirred for 30 minutes, and about 100 parts by volume of a saturated aqueous sodium bicarbonate solution is added. The mixture is concentrated under reduced pressure. The resulting crystals are collected by filtration, washed with water and dried to give 8-chloro-1-methyl-6-phenyl-4H-s-triazolo[4,3-a][1,4]benzodiazepine as colorless crystals. Recrystallization from acetone-n-hexane gives colorless needles melting at 226°–227° C.

| Elementary Analysis | | | |
|---|---|---|---|
| Calculated for $C_{17}H_{13}ClN_4$ | C 66.39, | H 4.08, | N 18.07 |
| Found | C 66.13, | H 4.24, | N 18.15 |

REFERENCE 3

2-Hydrazino-7-nitro-5-phenyl-3H-1,4-benzodiazepine is reacted in chloroform with ethyl orthoformate in the presence of p-toluenesulfonic acid. Subsequently the same procedure applies correspondingly as is described in Reference 2, whereupon 8-nitro-6-phenyl-4H-s-triazolo[4,3-a][1,4]benzodiazepine is produced as pale yellow needles melting at 271°–272° C.

REFERENCE 4

The same procedure as is described in Reference 2 is carried out by employing ethyl orthoacetate in place of ethyl orthoformate, whereupon 1-methyl-8-nitro-6-phenyl-4H-s-triazolo[4,3-a][1,4]benzodiazepine is obtained as yellow prisms melting at 227°–229° C.

REFERENCE 5

3.3 Parts of 2-(2-acetylhydrazino)-7-chloro-5-phenyl-3H-1,4-benzodiazepine is melted by heating at 215° C for 10 minutes under weakly reduced pressure. After cooling, the resultant is recrystallized from ethyl acetate to give 8-chloro-1-methyl-6-phenyl-4H-s-triazolo[4,3-a][1,4]benzodiazepine as colorless needles melting at 225°–226° C. The product coincides with that produced in Reference 2.

REFERENCE 6

To a solution of 1.6 parts of 7-chloro-2-hydrazino-5-(4-methoxyphenyl)-3H-1,4-benzodiazepine in 50 parts by volume of ethanol is added 3 parts of ethyl orthoformate. To the mixture is added 0.5 part by volume of concentrated sulfuric acid with stirring. After 5 minutes, the reaction mixture is neutralized with a saturated aqueous sodium bicarbonate solution, followed by removal of the solvent. To the residue is added water, whereupon 8-chloro-6-(4-methoxyphenyl)-4H-s-triazolo[4,3-a][1,4]benzodiazepine is obtained as crystals. Recrystallization from acetone-ethyl acetate gives pale yellow flakes melting at 216°-217° C.

REFERENCE 7

The same procedure as is described in the preceding Reference is carried out by employing ethyl orthoacetate in place of ethyl orthoformate, whereupon 8-chloro-1-methyl-6-(4-methoxyphenyl)-4H-s-triazolo[4,3-a][1,4]benzodiazepine is obtained as crystals. Recrystallization from methanol-chloroform yields colorless needless melting at 268°-269° C.

What we claim is:

1. A process for producing a compound of the formula

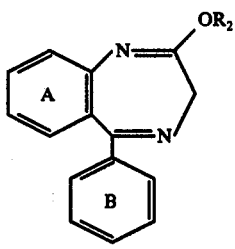

wherein $R_2$ is lower alkyl and each of rings A and B is unsubstituted or substituted by a member selected from the group consisting of nitro, trifluoromethyl, halogen, alkyl having up to 4 carbon atoms and alkoxy having up to 4 carbon atoms, which consists essentially of reacting a compound of the formula

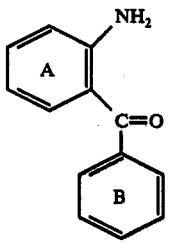

wherein rings A and B are as defined above, with a compound of the formula $XCH_2C(OR_2)_3$ wherein X is halogen and $R_2$ is as defined above, isolating and reacting the resultant compound of the formula

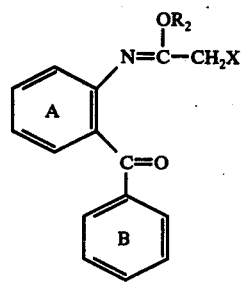

wherein X, $R_2$ and rings A and B are as defined above, with a compound of the formula $MN_3$ wherein M is an alkali metal, and isolating and subjecting the resultant compound of the formula

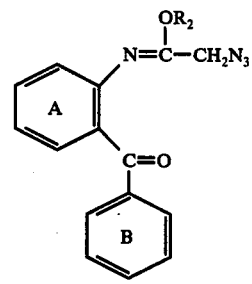

wherein $R_2$ and rings A and B are as defined above, to reductive ring-closure in the presence of a solvent and a reducing agent selected from the group consisting of (1) a compound of the formula $P(R_4)_3$ wherein $R_4$ is alkyl having 1-4 carbon atoms, benzyl or phenyl, and (2) a combination of zinc powder and aqueous ammonium chloride, at a temperature of from room temperature to the boiling point of the solvent.

2. A process for producing 2-ethoxy-7-nitro-5-phenyl-3H-1,4-benzodiazepine which consists essentially of reacting 2-amino-5-nitrobenzophenone with ethyl orthobromoacetate, isolating and reacting the resultant 2-(2-bromo-1-ethoxyethylideneamino)-5-nitrobenzophenone with sodium azide and isolating and reducing the resultant 2-(2-azido-1-ethoxyethylideneamino)-5-nitrobenzophenone in the presence of a solvent and triphenylphosphine at a temperature of from room temperature to the boiling point of the solvent.

3. A process for producing 7-chloro-2-ethoxy-5-(4-methoxyphenyl)-3H-1,4-benzodiazepine which consists essentially of reacting 2-amino-5-chloro-4'-methoxybenzophenone with ethyl orthobromoacetate, isolating and reacting the resultant 2-(2-bromo-1-ethoxyethylideneamino)-5-chloro-4'-methoxybenzophenone with sodium azide and isolating and reducing the resultant 2-(2-azido-1-ethoxyethylideneamino)-5-chloro-4'-methoxybenzophenone in the presence of a solvent, zinc powder and an aqueous solution of ammonium chloride at a temperature of from room temperature to the boiling point of the solvent.

* * * * *